United States Patent [19]

Buren

[11] 4,396,414
[45] Aug. 2, 1983

[54] METHOD OF INCREASING THE YIELD OF LEGUMES UTILIZING CHLOROACETYLAMINO-1,3-DIOXANES

[75] Inventor: Lawrence L. Buren, Cupertino, Calif.

[73] Assignee: Stauffer Chemical Company, Westport, Conn.

[21] Appl. No.: 277,562

[22] Filed: Jun. 25, 1981

[51] Int. Cl.³ .............................................. A01N 43/00
[52] U.S. Cl. ......................................... 71/88; 549/371
[58] Field of Search ............................................. 71/88

[56] References Cited

U.S. PATENT DOCUMENTS

| | | | |
|---|---|---|---|
| 4,221,584 | 9/1980 | Riman | 71/88 |
| 4,276,078 | 6/1981 | Pallos et al. | 71/88 |
| 4,294,764 | 10/1981 | Rinehart | 71/88 |
| 4,336,058 | 6/1982 | Felix | 71/88 |

Primary Examiner—Ethel G. Love
Attorney, Agent, or Firm—Edwin H. Baker

[57] ABSTRACT

A method of increasing the yield of legumes (soybeans) utilizing a compound of the formula

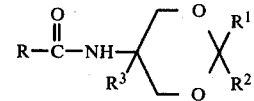

where R is chloromethyl or dichloromethyl; $R^1$ is lower alkyl, vinyl or phenyl; $R^2$ is hydrogen or lower alkyl and $R^3$ is hydrogen or lower alkyl.

10 Claims, No Drawings

METHOD OF INCREASING THE YIELD OF LEGUMES UTILIZING CHLOROACETYLAMINO-1,3-DIOXANES

BACKGROUND OF THE INVENTION

According to the method of the present invention, the yield of certain plants, particularly crop plants, can be improved by applying to such plants a yield-improving amount of certain chloroacetylamino-1,3-dioxanes, described herein. The plants for which the present invention has been found especialy useful are the legumes, e.g., soybeans, peas, peanuts and clover.

The application of the certain chloroacetylamino-1,3-dioxanes improve the yield of legumes as much as about 30 percent. The term "yield" means dry weight of harvested pods of the legume crop plants. The yield per plant and the yield per acre is improved by application of the compound of this invention.

The term "soybean" includes both the determinate type (e.g. Bragg) which is grown in the southern United States, and the indeterminate type (e.g. Corsoy or Williams) which is grown in the northern United States and Canada. Generally, the determinate varieties of soybeans grow very little after flowering, if at all, and branch more profusely than indeterminate varieties. Indeterminate varieties increase their height by two to four times after flowering begins.

DESCRIPTION OF THE INVENTION

The compounds that are useful in the practice of this invention are certain known chloroacetylamino-1,3-dioxanes having the following structural formula

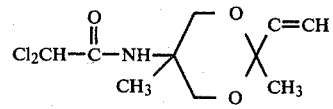

wherein
R is chloromethyl or dichloromethyl;
$R^1$ is $C_1$–$C_4$ alkyl, preferably $C_1$–$C_2$ alkyl, vinyl or phenyl;
$R^2$ is hydrogen or $C_1$–$C_4$ alkyl, preferably $C_1$–$C_2$ alkyl; and
$R^3$ is hydrogen or $C_1$–$C_4$ alkyl, preferably methyl.

The compounds useful in the practice of this invention are known and are described in U.S. application Ser. No. 271,899, filed June 16, 1981. Also described in this U.S. application is a method of synthesis for the compounds.

The chloroacetylamino-1,3-dioxanes of this invention can be prepared according to the following general procedures, depending upon the starting materials.

In a first procedure, an appropriate chloromethylcarbonyl chloride is reacted with 5-methyl-5-amino-1,3-dioxane in a basic solution. The reaction is carried out at temperatures below 35° C. The reaction mixture is stripped and the product recrystallized in ethanol/water. Structure can be confirmed by nuclear magnetic resonance (NMR) spectroscopy.

In an alternate procedure, an appropriate dialkoxy compound is reacted with an appropriate dihydroxyalkyl haloacetamide in an acidic solution. The reaction is carried out at elevated temperatures. Distillate is collected at 80° C. The distillate is cooled and washed with sodium carbonate and water. The product is obtained by removing the solvent in vacuum. Structure can be confirmed by NMR spectroscopy.

The following example illustrates the preparation of a specific compound according to the second general method. (The compound number corresponds to that used in Tables I and II.)

EXAMPLE I (Compound No. 6)

Preparation of 2-vinyl-5-methyl-5-dichloroacetylamino-1,3-dioxane

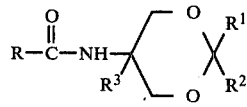

This example illustrates use of the alternate general procedure.

Six and one-half grams (g) (0.03 mole) of 2,2-(dimethoxyethyl) dichloroacetamide, 3.9 g (0.03 mole) of acrolein diethylacetal, 50 ml of acetonitrile and 0.2 g of ammonium chloride were combined in a reaction flask. The reaction mixture was stirred and refluxed through an attached packed column and variable take-off condenser. Distillate was removed to a head temperature of 78° C.

The reaction mixture was cooled to 40° C. and 0.1 g of crushed ammonium chloride was added. The mixture was heated to reflux and distillate was collected between 73° and 81° C. An additional 0.1 g of ammonium chloride was added and the temperature rose to 83° C. Heating was stopped and the hot reaction mixture was poured over ice and extracted twice with 75 ml of dichloromethane. The extracts were combined and washed with 100 ml of water. After drying, the solvent was removed in vacuo to yield 5.0 g of 2-vinyl-5-methyl-5-dichloroacetalamino-1,3-dioxane, an oil. $n_D^{30} = 1.4980$. Structure was confirmed by NMR spectroscopy and gas chromatography.

The following is a table of certain selected compounds that are useful in the practice of this invention. These compounds are preparable according to the general and specific procedure described herein. Compound numbers are assigned to each compound and are used throughout the remainder of this application.

TABLE I

| Cmpd. No. | R | $R^1$ | $R^2$ | $R^3$ | m.p. or $n_D^{30}$ |
|---|---|---|---|---|---|
| 1 | $Cl_2CH$ | $CH_3$ | $C_2H_5$ | $CH_3$ | 84–87° C. |
| 2 | $ClCH_2$ | $CH_3$ | $CH_3$ | $C_2H_5$ | 67–70° C. |
| 3 | $Cl_2CH$ | $CH_3$ | $CH_3$ | $C_2H_5$ | 90–93° C. |
| 4 | $ClCH_2$ | $C_2H_5$ | $CH_3$ | $CH_3$ | 62–69° C. |
| 5 | $ClCH_2$ | $CH_2{=}CH$ | H | $CH_3$ | 78–83° C. |
| 6 | $Cl_2CH$ | $CH_2{=}CH$ | H | $CH_3$ | 1.4980 |
| 7 | $ClCH_2$ | phenyl | H | $CH_3$ | >190° C. |
| 8 | $Cl_2CH$ | phenyl | H | $CH_3$ | 145–148° C. |

EVALUATION TEST ON SOYBEANS

The purpose of this test is to evaluate compounds for soybean pod weight increase. Selected compounds of this invention are evaluated for such weight increase in the following manner.

Round fiber pots (6 inches in diameter) are filled with screened, sandy loam soil which has been fortified with 17-17-17 granular fertilizer to yield a soil mix having 150 parts per million (ppm) each of nitrogen, $P_2O_5$ and $K_2O$. Soybean seeds of either the determinate or indeterminate type are planted in the soil about 0.5 inches deep in a single row in sufficient number that 10–15 seedlings are obtained. After the seedlings have reached a unifoliate leaf stage they are thinned to four plants per pot.

Several such pots are retained as controls and other pots are treated with a candidate compound. The time of treatment of the four plants is between an early vegetative state and an early flowering state. The plants are treated with a compound by placing a pot on a linear spray table and spraying with 25 gallons per acre (235 liters per hectare) of an appropriate concentration of chemical compound to yield a treatment of ⅛, ½, 1 or 3 pounds per acre (lb/A) (8.75, 35, 70, or 210 grams per hectare). The compounds are dissolved in a 1:1 acetone-$H_2O$ mixture containing 0.5 percent polyoxyethylene sorbitan monolaurate emulsifier prior to the treatment.

The treated and untreated control plants are placed in a glasshouse and maintained at a temperature of approximately 70° F. at night and 80°–85° F. during the day. The plants are fertilized twice during the crop cycle with 1:1:1 ratio of a nitrogen, $P_2O_5$, $K_2O$ fertilizer solution (3.4 grams nitrogen, $P_2O_5$, $K_2O$ per liter of water). Normally 70 milliliters (ml) of this solution is added to each pot at each of the two fertilization times. Usually these fertilization times are at one and two months after seeding.

Evaluation is made after the plants have fully matured, i.e., when the leaves and pods have senesced. The term "pods" as used herein means pods with beans. The pods are removed from the treated plants, dried in a forced-air dryer at 120° F. to a constant weight, i.e., until all moisture is evaporated from the pods. Next, the dry weight of the pods is ascertained and compared to the dried weight of pods from an untreated plant.

The percent increase in pod weight is calculated and is reported in Table II.

TABLE II

| Compound Number | Treatment Rate lb/A | Percent Increase in Pod Dry Weight |
|---|---|---|
| 1 | ⅛ | 2 |
|   | ½ | 9 |
|   | 1 | 6 |
| 2 | 3* | 6 |
| 3 | ⅛ | 25 |
|   | ½ | 28 |
|   | 1 | 23 |
| 4 | ⅛ | 2 |
|   | ½ | 13 |
|   | 1 | 11 |
| 5 | ⅛ | 12 |
|   | ½ | 15 |
|   | 1 | 12 |
| 6 | ⅛ | 4 |
|   | ½ | 8 |
|   | 1 | 7 |
| 7 | ⅛ | 6 |
|   | ½ | 11 |
|   | 1 | 12 |
| 8 | ⅛ | 11 |
|   | ½ | 2 |
|   | 1 | (−4) |

*Not evaluated at lower rates.

Application of the chloroacetylamino-1,3-dioxanes of this invention may be made employing the procedures normally used for treatment of plants including dip or soak treatment of tubers, bulbs or cuttings, for example, as well as foliar, bark or stem or soil application. Preferably the compounds are applied in a post-emergence foliar application, more preferably the compounds are applied directly to the plant between about 4 weeks prior to flowering and about 2 weeks after flowering of the plant. Flowers are produced where leaf petioles join the main stem or branches of the main stem. The active ingredient may be utilized in diverse formulations, including the adjuvants and carriers normally employed for facilitating the dispersions of active ingredients for agricultural applications, recognizing the known fact that the formulations and mode of application of a chemical agent may affect its activity in any given application. Thus, chloroacetylamino-1,3-dioxanes can be formulated as a solution or dispersion in a non-aqueous medium, as a powdery dust, as a wettable powder, as an emulsifiable concentrate, as a granule or as any of several other known types of formulations, depending upon the desired mode of application. These growth regulatory compositions may be applied as dusts, sprays, dips or granules in the sites in which growth regulation is desired. These formulations may contain as little as 0.0005% or as much as 95% or more by weight of active ingredient and applications may be at rates of about 1/32 to about 5 pounds per acre, preferably about 1/16 to about 2 pounds per acre.

Dusts are admixtures of the active ingredient with finely-divided solids such as talc, attapulgite clay, kieselguhr and other organic and inorganic solids which act as dispersants and carriers for the regulant. These finely divided solids have an average particle size of less than 50 microns. A typical dust formulation useful herein is one containing 1.0 part of chloroacetylamino-1,3-dioxane and 99.0 parts of talc.

Wettable powders are in the form of finely divided particles which disperse readiy in water or other dispersant. The wettable powder is ultimately applied to the plant either as a dry dust or as an emulsion in water or other liquid. Typical carriers for wettable powders include fuller's earth, kaolin clays, silicas, and other highly absorbent, readily wet inorganic diluents. Wettable powders normally are prepared to contain about 5% to 80% of active ingredient, depending upon the absorbency of the carrier and usually also contain a small amount of a wetting, dispersing or emulsifying agent to facilitate dispersion.

Other useful formulations for plant applications are the emulsifiable concentrates which are homogeneous liquid or past compositions which are dispersable in water or other dispersant and may consist entirely of chloroacetylamino-1,3-dioxane with a liquid or solid or emulsifying agent or may also contain a liquid carrier such as xylene, heavy aromatic naphthas, isophorone and other non-volatile organic solvents. For plant application, these concentrations are dispersed in water to other liquid carrier and normally applied as a spray to the area to be treated. The percentage of weight of the essential active ingredient may vary according to the manner in which the composition is to be applied, but in general, comprises 0.005% to 95% of active ingredient.

Other useful formulations include simple solutions of the active ingredient in a dispersant in which it is completely soluble at the desired concentration, such as acetone or other organic solvents. Granular formulations wherein the chemical agent is carried on relatively coarse particles are of particular utility for aerial distribution or for penetration of cover crop canopy. Pressurized sprays, typically aerosols wherein the active ingredient is dispersed in finely-divided form as a result of vaporization of low boiling dispersant solvent carrier such as the freons, may also be used.

Of course, the formulations, concentration and mode of application of chloroacetylamino-1,3-dioxanes will be adapted to the particular plant and surrounding circumstances as is the case in all agronomic applications.

The active growth regulatory compound of this invention may be formulated and/or applied with other agricultural chemicals, such as insecticides, fungicides, nematocides, fertilizers and the like. In addition, combinations of chloroacetylamino-1,3-dioxanes with certain plant hormones, such as native auxins, anti-auxins, giberellins and kinins, may produce enhanced growth regulatory effects.

I claim:

1. A method of increasing the yield of legumes comprising applying thereto a yield-increasing amount of a compound of the formula 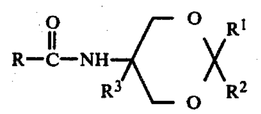 wherein R is chloromethyl or dichloromethyl;

$R^1$ is $C_1$–$C_4$ alkyl, vinyl or phenyl;

$R^2$ is hydrogen or $C_1$–$C_4$ alkyl; and $R^3$ is hydrogen or $C_1$–$C_4$ alkyl.

2. The method of claim 1 wherein the legume is soybeans.

3. The method of claim 2 wherein the yield-increasing amount of said compound is between about 1/32 to about 5 pounds per acre.

4. The method of claim 2 wherein the yield-increasing amount is applied between about 4 weeks prior to flowering of the soybeans plant and 2 weeks after said flowering.

5. The method of claim 2 wherein the yield-increasing amount of said compound is between about 1/16 to about 2 pounds per acre.

6. The method of claim 4 wherein the yield-increasing amount of said compound is between 1/16 to about 2 pounds per acre.

7. The method of claim 3 wherein R is chloromethyl, $R^1$ is methyl, $R^2$ is ethyl, and $R^3$ is methyl.

8. The method of claim 6 wherein R is chloromethyl, $R^1$ is methyl, $R^2$ is ethyl, and $R^3$ is methyl.

9. The method of claim 6 wherein R is chloromethyl, $R^1$ is methyl, $R^2$ is methyl, and $R^3$ is ethyl.

10. The method of claim 6 wherein R is chloromethyl, $R^1$ is $C_1$–$C_2$ alkyl, vinyl, or phenyl, $R^2$ is hydrogen or $C_1$–$C_2$ alkyl, and $R^3$ is hydrogen or methyl.

* * * * *